United States Patent [19]

Friend

[11] 4,175,923
[45] Nov. 27, 1979

[54] METHOD AND APPARATUS FOR OCCULT BLOOD TESTING IN THE HOME

[76] Inventor: William G. Friend, 9039 SE. 59th, Mercer Island, Wash. 98040

[21] Appl. No.: 919,395

[22] Filed: Jun. 26, 1978

[51] Int. Cl.² .................... G01N 21/20; G01N 33/16
[52] U.S. Cl. ............................ 23/230 B; 252/408; 422/56; 422/61
[58] Field of Search .............. 23/230 B, 253 TP; 422/56, 61

[56] References Cited

U.S. PATENT DOCUMENTS

| | | | |
|---|---|---|---|
| Re. 28,575 | 10/1975 | Bauer | 252/408 |
| 2,290,436 | 7/1942 | Kamlet | 23/230 B |
| 2,799,660 | 7/1957 | Nicholis | 252/408 |
| 2,838,377 | 6/1958 | Fonner | 23/230 B |
| 3,012,976 | 12/1961 | Adams | 252/408 |
| 3,092,463 | 6/1963 | Adams | 23/253 |
| 3,092,464 | 6/1963 | Adams | 23/253 |
| 3,252,762 | 5/1966 | Adams | 23/253 |
| 3,290,117 | 12/1966 | Adams | 23/253 |
| 3,627,697 | 12/1971 | Rey | 252/408 |
| 3,627,698 | 12/1971 | Rey | 252/480 |
| 3,630,957 | 12/1971 | Rey | 252/408 |
| 3,654,179 | 4/1972 | Bauer | 252/408 |
| 3,672,351 | 6/1972 | Ubersax | 128/2 G |
| 3,713,772 | 1/1973 | Tavel | 23/230 B |
| 3,718,431 | 2/1973 | Wild | 23/230 B |
| 3,853,471 | 12/1974 | Rittersdorf | 23/230 B |
| 3,853,472 | 12/1974 | Rittersdorf | 23/230 B |
| 3,917,452 | 11/1975 | Rittersdorf | 23/230 B |
| 3,975,161 | 8/1976 | Svoboda | 23/253 |
| 3,986,833 | 10/1976 | Mast | 23/230 B |
| 3,996,006 | 12/1976 | Pagano | 23/253 TP |
| 4,005,984 | 2/1977 | Alsop | 23/230 B |
| 4,017,261 | 4/1977 | Svoboda | 23/253 TP |
| 4,061,468 | 12/1977 | Lange | 23/253 TP |
| 4,063,984 | 12/1977 | Ogawa | 23/253 TP |
| 4,092,120 | 5/1978 | Svovaniemi | 23/253 TP |

OTHER PUBLICATIONS

Miller, Sidney F., CA-A Cancer Jour. for Clinicians, vol. 27(6), 338–343 (1977).
Sherlock; P. et al., Digestive Diseases, vol. 19(10), 959–964 (1974).
Chemical Abstracts, 66:8780e, 8781n (1967).

*Primary Examiner*—Sidney Marantz
*Attorney, Agent, or Firm*—Christensen, O'Connor, Johnson & Kindness

[57] ABSTRACT

A method for determining the presence of occult blood in the bowl of a toilet containing water and fecal matter includes the steps of applying a developing solution to a sheet of absorbent paper impregnated with a guaiac reagent to form an activated test sheet of paper, and contacting the test paper with the water in the toilet bowl. Preferably, the test sheet is an absorbent paper impregnated with a guaiac reagent and having only a portion thereof additionally impregnated with blood in an amount sufficient to react with the guaiac in the presence of a developing solution to dye the paper blue. The blood impregnated portion of the sheet upon use forms a dyed test strip with which the person using the paper can make a comparison to determine whether and the extent to which the actual guaiac reaction has taken place on the remaining portion of the sheet.

15 Claims, 3 Drawing Figures

METHOD AND APPARATUS FOR OCCULT BLOOD TESTING IN THE HOME

BACKGROUND OF THE INVENTION

The present invention relates to a method and apparatus for testing to determine the presence of occult blood in fecal matter, and more particularly to a method and apparatus for testing to determine the presence of occult blood in the private environment of a person's home without the necessity of handling the fecal matter prior to or during the test procedure and for eliminating handling of the test materials once the test is completed.

Over 100,000 persons in the United States are affected by cancer of the colon and rectum per year, occurring equally in both the male and female. When the number of colorectal cancers occurring each year is combined with the number of cancers occurring in other digestive organs, including the esophagus and stomach, such cancers of the digestive system account for more occurrences of cancer than any other single form of the disease. Contrary to many other forms of cancer, early diagnosis and treatment of digestive tract cancer does result in a cure rate of 80% to 90% of those persons affected by the disease. If, however, the disease is not detected until the later stages, the cure rate drops drastically to 25% or less. Thus early detection of the disease is critical to successful treatment of digestive tract cancer.

Most, but not all cancers of the digestive tract bleed to a certain extent. This blood is deposited on and in fecal matter excreted from the digestive system. The presence of blood in fecal matter is not normally detected, however, until gross bleeding, that is, blood visible to the naked eye, occurs. Most advance cancers cause gross bleeding.

It is known that digestive tract cancers in the early stages also tend to bleed, giving rise to occult (hidden) blood in the fecal matter. Test equipment and test procedures have been developed for use by physicians in testing for the presence of occult blood in fecal matter. One of the most successful tests is manufactured and sold by Smith Kline Diagnostics, a division of Smith Kline Instruments, Inc. of Sunnyvale, California under the trademark Hemoccult and disclosed in U.S. Pat. No. 3,996,006 issued to J. F. Pagano. Briefly, the Pagano test employs an absorbent paper impregnated with a guaiac reagent and encased in a special test slide having openable flaps on both sides of the test slide. To use the Pagano test slide, the physician or a lab technician must obtain a sample of fecal matter, smear it onto the guaiac impregnated paper by opening the panel on one side of the test slide, and thereafter close the panel. A panel on the opposite side of the test slide is then opened and a nonaqueous developing agent is applied to the guaiac impregnated paper. If occult blood is present in the fecal matter smeared on the opposite side of the paper, the guaiac reaction will dye the paper blue, providing a positive indication of the presence of blood in the fecal matter.

Although the Pagano test is excellent for use by physicians in their offices and by diagnostic laboratories, it is not the type of test which is readily adaptable for use by the ordinary person because of his adverse reaction to handling fecal matter. As stated above, the Pagano test requires that a specimen of fecal matter be obtained. Normally a specimen is obtained by procuring a sample on the end of a spatula or a wooden depressor, which is then used to smear the specimen on the paper in the Pagano test slide. Once the sample is obtained and the test procedure completed, both the test slide and the spatula or depressor must be disposed of. Disposal of the used materials can and does present a physical problem to, if not an adverse psychological reaction from, the ordinary person. Thus, the ordinary person is not likely to use the Pagano test because of its uncleanly nature (at least apparently so to the ordinary person) and because of the disposal problems associated with the used test slide and spatula or depressor. Additionally, the ordinary person does not necessarily have the skill required to analyze, and thus form accurate conclusions from, the test results.

It has also been suggested that the ordinary person could initiate the Pagano test in his home and then forward the test slide to his physician or a laboratory for addition of the developing agent and analysis of the test. This procedure however, is not viable as it requires cold storage of the test slide and specimen if there is a significant time lapse before the test can be completed. Certainly, the ordinary person does not wish to store a fecal specimen in his household refrigerator, normally the only cold storage available to him, until he can present the specimen to his physician or an appropriate laboratory.

Another test for occult blood is suggested by D. E. Fonner in U.S. Pat. No. 2,838,377. The Fonner test as disclosed can be effected in a toilet bowl containing fecal matter. The basic test reagents employed by Fonner are o-tolidine, o-toluidine, and benzidine. These reagents in the presence of blood and other reactants produce a dye visible to the naked eye. Although the Fonner test appears to be a solution to the problem of finding a viable home test for occult blood, it has not met with success for two reasons. First, the above-listed reagents are in themselves known to cause cancer and thus are not suitable for general public distribution. Additionally, the Fonner reagents have a relatively high rate of providing false indications of the presence of occult blood.

Thus, to date, the use of the Pagano test, the Fonner test and other similar tests has been limited primarily to physicians and diagnostic laboratories or has proven unworkable or unreliable. Although this limitation might not at first glance present a significant problem, it does limit the early detection of digestive tract cancers, primarily because patients will not see a physician until other symptoms of digestive tract cancers, such as gross bleeding, manifest themselves. Thus, early detection of cancer of the digestive tract still does not occur with the majority of patients who contract the disease.

It is therefore a broad object of the present invention to increase the early detection rate of cancers of the digestive tract. It is a further object of the present invention to provide a test method and apparatus that can be employed by the ordinary person, preferably in his own home on a periodic basis, to determine the presence of occult blood in the person's fecal matter. It is a further object of the present invention to provide such test methods and apparatus that do not require the patient to handle his fecal matter during the test procedure and to provide test procedures and apparatus that do not have to be handled during performance of the test and do not have to be handled for disposal. It is another object of the invention to provide such test methods and apparatus that are easily conducted and understood by the ordinary person and that will provide an easily recognizable, analyzable, reproducible, and reliable test result.

SUMMARY OF THE INVENTION

In accordance with the foregoing objects, and other objects that will become apparent to one of ordinary skill in the art after reading the following specification, the present invention provides a method for determining the presence of occult blood in the bowl of a toilet containing water and fecal matter. In its broadest sense, the method simply comprises the two steps of applying a developing solution to a sheet of absorbent paper, or other absorbent substrate, impregnated with guaiac reagent to form an activated test paper, and contacting the test paper with the water in the toilet bowl. If occult blood is present in the water, the guaiac will react in the presence of the developing solution and blood to produce a blue dye, which will visibly stain the test paper. Although this test method is relatively simple and straightforward, especially in view of the prior test procedures available to physicians, the test procedure of the present invention was made possible primarily by the recognition of two factors. First, guaiac is known to be insoluble in water. Thus, the use of a guaiac reagent in a cold water environment such as that encountered in a toilet bowl was felt to be virtually impossible. Second, it was not recognized that the occult blood present in fecal matter would disperse into water, for example, water in a toilet bowl, in amounts sufficient to trigger the guaiac dye-producing reaction. As disclosed herein, however, it has been found that the use of a developing solution that contains a carrier that is soluble in water and in which guaiac is soluble will allow the guaiac reaction to proceed in a relatively cold aqueous environment. Moreover, it has been found that sufficient occult blood disperses into the water in the toilet bowl from fecal matter and migrates to the water surface in the toilet bowl so that the guaiac impregnated absorbent paper of the present invention need only be allowed to float on the top of the water in the toilet bowl in order for the dye-producing reaction to effectively proceed.

Thus, the foregoing method of the present invention allows an individual in the privacy of his own home to test for the presence of occult blood in his fecal matter. More importantly, the test of the present invention does not require the person to in any way handle the fecal matter before, during or after the test is performed. Further, no spatulas or depressors are needed to conduct the test. After the test is conducted, only the test paper remains, which can easily be flushed down the toilet without adverse effect on a domestic plumbing system.

More preferably, the absorbent test paper of the present invention that has been impregnated with guaiac also has a portion thereof impregnated with blood, for example, human or animal blood. When the developing solution is placed on the test paper, the blood on the portion of the test paper will immediately react with the guaiac to dye that portion of the paper blue. Thus when the person contacts the paper with the water in the toilet bowl, a portion of the paper will automatically be dyed blue. Advantageously, the test strip first allows the user to be assured the test is actually working as it is supposed to be. Secondly, and perhaps more importantly, a direct visual comparison can be made between the dyed portion caused by the presence of the preimpregnated blood and a dye stain appearing on the remaining portion of the paper that is caused by occult blood present in the toilet water. Consequently, the preferred form of the invention leaves little chance of the ordinary person misreading or misinterpreting the results of the test.

Preferably, the test procedure and apparatus is made available to a person in the form of a home test kit. The kit comprises at least one sheet of paper impregnated with a guaiac reagent. A portion of the sheet of paper is additionally impregnated with animal blood, or other material, that will react with guaiac to dye the test paper blue in the same manner as occult blood. Additionally, the test kit will comprise a receptacle containing a developing solution that, when applied to the paper and thereafter contacted with occult blood, will cause the guaiac to react with the blood to dye the paper blue. Preferably, the developing solution comprises an alcohol and a peroxide.

BRIEF DESCRIPTION OF THE DRAWINGS

A better understanding of the present invention can be derived by reading the ensuing specification in conjunction with the accompanying drawings, wherein.

DETAILED DESCRIPTION OF THE INVENTION

Figure 1:
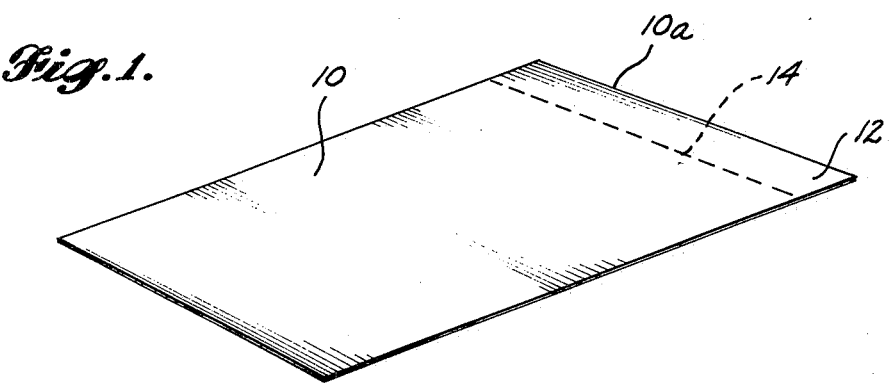
FIG. 1 is an isometric view of the preferred absorbent test paper of the present invention.

Referring first to FIG. 1, a sheet 10 of absorbent paper impregnated with guaiac, a commonly known reagent that undergoes a reaction with certain components in blood in the presence of a developing solution to form a blue dye, is formed into a convenient size for handling, for example, on the order of 3" by 4". The paper can be any of a wide variety of absorbent types, including an absorbent laboratory filter paper. Guaiac impregnated paper suitable for use in accordance with the present invention is commercially available. In accordance with the present invention, one portion 12 of the sheet is also impregnated with the components of blood that will react with the guaiac in the paper in the presence of a developing solution. As will be understood, the portion 12 of the sheet preimpregnated with blood will form a comparison strip against which the ordinary person uninitiated in occult blood testing can visually compare the test results.

A preferred method of impregnating portion 12 of the sheet with blood is to dissolve commercially available dried human or animal blood in a solvent such as water. Blood can be mixed with water in weight proportions from 1:1 to 1:5000 and, preferably, from 1:50 to 1:1000, blood to water. In the foregoing amounts, the guaiac dye-producing reaction will always occur on the test portion 12 of the sheet once the developing solution is applied as disclosed below. Once the blood is dissolved in the water, the end of the paper can be dipped in the blood solution up to a point indicated by the dotted line 14. The solvent is then allowed to evaporate from the paper, leaving the dried blood embedded in the strip of the paper between the dotted line 14 and the end 10a of the test strip.

Figure 2:
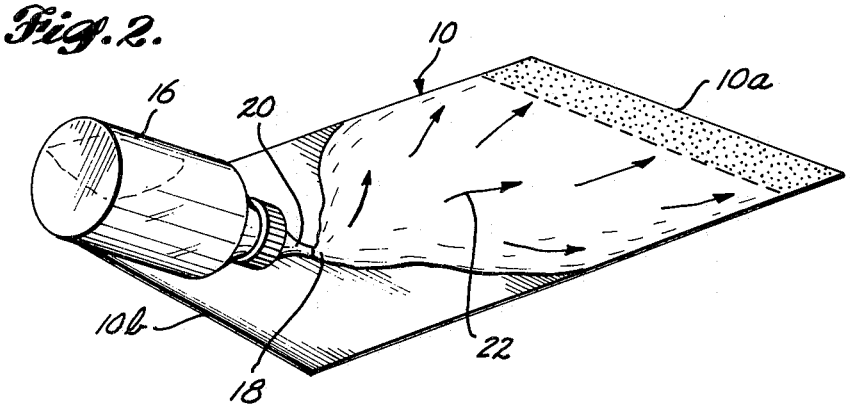
FIG. 2 is an isometric view of the test paper with the developing solution being applied thereto.

Referring to FIG. 2, when the test strip is ready for use, it is saturated with a developing solution. The developing solution can be deployed onto the test sheet 10 from a flexible polyethylene bottle 16 or other suitable container. As shown in FIG. 2, the developing solution 18 is ejected from the nozzle 20 of the bottle 16 as the bottle is moved from one end 10a of the test sheet toward the other end 10b of the test sheet. As the developing solution is ejected from the bottle along the center of the strip, it migrates toward the sides of the strip in the direction of arrows 22. A suitable developing solution for use with the guaiac impregnated in the sheet is a commercially available alcohol and a peroxide, such as a mixture of denatured ethyl alcohol and hydrogen peroxide.

Figure 3:
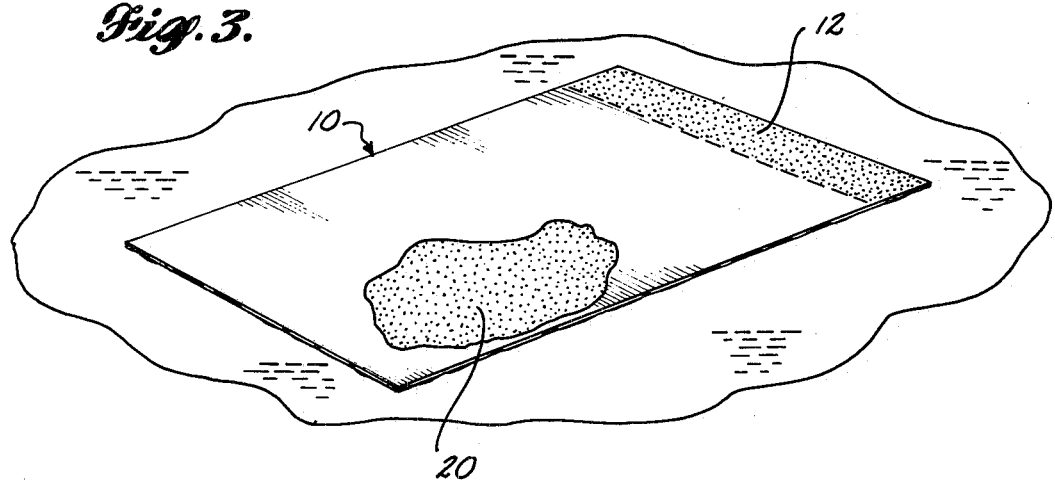
FIG. 3 is an isometric view of the test paper floating on the aqueous environment being tested.

Once the developing solution is absorbed by the test paper and therefore in intimate contact with the guaiac in the paper, the paper can be deposited on the surface of the water in a toilet bowl containing fecal matter, as illustrated in FIG. 3. Almost as soon as the developing solution is placed on the paper, the blood impregnated comparison strip (portion 12 of the paper) will turn blue, which is caused by the blood/guaiac reaction producing a blue dye. If there is occult blood present in the water of the toilet bowl, the guaiac will react with the blood absorbed into the paper from its bottom side and will yield the blue dye. The blue dye is sufficiently strong to permeate the test paper and be easily visible on the top of the paper, as for example the positive blue dyed patch on the paper indicated by reference numeral 20. The strip on portion 12 of the test paper thus not only provides an indication that the guaiac reaction is working, but also forms a basis for visually comparing any reaction that occurs due to the presence of occult blood in the toilet bowl water with the similar reaction of the animal blood and the guaiac in the comparison strip. Thus the presence of the blue dye from the animal blood reaction will allow the ordinary person to readily distinguish any spurious reaction that might occur in the remaining portions of the test paper from those that are associated with the reaction of occult blood in the water. If no occult blood is present in the remaining portion of the test paper, the test paper will remain its original color, normally white.

After the occult blood test is completed, which normally takes on the order of only a few seconds to less than one minute, the toilet water can be flushed into the sewer system. The test paper will be flushed into the sewer system along with the water from the toilet bowl, thus eliminating any need to dispose of any of the test materials employed while conducting the occult blood test.

The test methods of the present invention can be easily conducted by the oridinary person in the privacy of his own home provided he has the requisite test materials. The requisite materials for conducting the test procedure include the guaiac impregnated paper, preferably with the portion impregnated with animal blood or a similar substance that will react with guaiac to produce a blue dye, and a container of developing solution. The test paper can be supplied in a plurality of sheets in a container along with the receptacle for the developing solution. In use, the kit can be employed on a periodic basis by taking a single sheet of the test paper, saturating it with developing solution and depositing it on the surface of water in a toilet containing fecal matter.

It may become desirable under certain circumstances in order to detect very minute amounts of occult blood that have migrated into the toilet water from the fecal matter to stir or otherwise agitate the water and fecal matter in the toilet bowl. It has been found that the water can be agitated either before or after the test sheet is deposited on the water. One easy method for agitating the water in the toilet bowl is to deposit a small amount of a composition of matter that, when contacted with water, will produce a gas or effervesce sufficiently to agitate the water and fecal matter. A suitable composition of matter for this purpose is a mixture of sodium bicarbonate and acetic acid, or any of a variety of other known substances that, upon contact with water, will produce a harmless gas that functions to agitate the toilet bowl water. The effervescing material is preferably deposited in the water in tablet form, again simplifying handling of the test materials.

As can be seen, the test methods of the present invention, as well as the apparatus employed to perform the test, fulfill the objects set forth above. Although the present invention has been described in relation to a preferred embodiment, one of ordinary skill in the art will be able to effect various changes, substitutions of equivalents and alterations to the methods and apparatus without departing from the broad concepts disclosed herein. It is therefore intended that the protection granted by Letters Patent hereon be limited only by the definition contained in the appended claims and equivalents thereof.

The embodiments of the invention in which an exclusive property or privilege is claimed are defined as follows:

1. A method for determining the presence of occult blood in the bowl of a toilet containing water and fecal matter comprising the steps of:
   applying a developing solution to an absorbent substrate impregnated with a guaiac reagent to form an activated test substrate,
   contacting the activated test substrate with the water in said toilet bowl, and
   observing whether a portion of the test substrate is dyed blue.

2. The method of claim 1 wherein said test substrate is placed on the surface of said water and allowed to float thereon.

3. The method of claim 1 further comprising the step of
   prior to applying said developing solution to said absorbent substrate, impregnating a predetermined portion of said substrate with blood that will react with guaiac in the presence of a developing solution to dye said substrate blue.

4. The method of claim 1 further comprising the step of agitating the water in said bowl prior to placing said substrate in said water.

5. The method of claim 1 further comprising the step of agitating the water in said bowl after placing said substrate in said water.

6. The method of claim 4 or 5 wherein said water is agitated by placing a composition of matter in said bowl which, upon contact with water, will chemically react to effervesce and agitate said water.

7. The method of claim 1 wherein said substrate comprises a sheet of absorbent paper.

8. A home test kit for determining the presence of occult blood in the bowl of a toilet containing water and fecal matter comprising:
   an absorbent substrate impregnated with a guaiac reagent, said absorbent substrate having only a portion thereof additionally impregnated with a composition that is present in said only portion of said absorbent substrate in an amount sufficient to react with said guaiac reagent in the presence of a developing solution to dye at least a portion of said substrate blue, and a receptacle containing a developing solution that, when applied to said substrate and thereafter contacted with blood, will cause said guaiac reagent to react and dye said substrate blue.

9. The kit of claim 8 wherein said composition comprises blood.

10. The kit of claim 8 wherein said developing solution comprises a peroxide solution.

11. The kit of claim 8 further comprising:

a composition that, upon contact with water, will effervesce to agitate the water in a bowl containing fecal matter.

12. The kit of claim 8 wherein said substrate comprises a sheet of absorbent paper.

13. A test substrate for use in determining the presence of occult blood comprising:

an absorbent substrate impregnated with a guaiac reagent, said substrate having only a portion thereof additionally impregnated with a composition that is present in said only portion of said substrate in an amount sufficient to react with said guaiac reagent in the presence of a developing solution to dye at least a portion of said substrate blue.

14. The test substrate of claim 13 wherein said composition comprises blood.

15. The test substrate of claim 13 wherein said absorbent substrate comprises a sheet of absorbent paper.

* * * * *